United States Patent [19]

Lindstrom

[11] Patent Number: 4,580,299
[45] Date of Patent: Apr. 8, 1986

[54] INTRAOCULAR LENS

[75] Inventor: Richard L. Lindstrom, Wayzata, Minn.

[73] Assignee: Surgidev Corp., Goleta, Calif.

[21] Appl. No.: 543,439

[22] Filed: Oct. 19, 1983

[51] Int. Cl.⁴ .................. A61F 1/16; A61F 1/24
[52] U.S. Cl. .................................................. 623/6
[58] Field of Search .................................. 3/13, 1

[56] References Cited

U.S. PATENT DOCUMENTS

| 4,403,354 | 9/1983 | Rainin | 3/13 |
| 4,426,741 | 1/1984 | Bittner | 3/13 |

OTHER PUBLICATIONS

Americal IOL International Intraocular Lenses (advertisement) Americal IOL International, 15542 Graham St. Huntington Beach, CA 92647 USA, Style 100 and Style 130 & 130A.
IOLAB Intraocular Lens Catalog (Jan. 4, 1982), IOLAB Corp. 861 South Village Oaks Drive, Corvina, CA 91724, 9 pages, Azar Design 91Z Lens.

Primary Examiner—Ronald L. Frinks
Attorney, Agent, or Firm—Hugh D. Jaeger

[57] ABSTRACT

One-size intraocular lens including a lens optic, one flexible secured loop and an other flexible free-end measured loop. Each loop assumes a U-shaped configuration and can be provided with an appropriate vault whether the lens is implanted into the anterior chamber or the posterior chamber. The lens and loop are constructed from a single monomer such as polymethylmethacrylate (PMMA) providing for stability, low mass, and flexibility in three degrees of freedom, particularly with respect to the ends. A lens template accompanies the lens for cutting the free end of the loop with the unsecured end to a predetermined length for engaging into the tapered hole for a subsequent mechanical frictional engagement therein. The loops are vaulted for a standard vault between the plane of the base of each loop and the plano surface of the lens optic.

8 Claims, 2 Drawing Figures

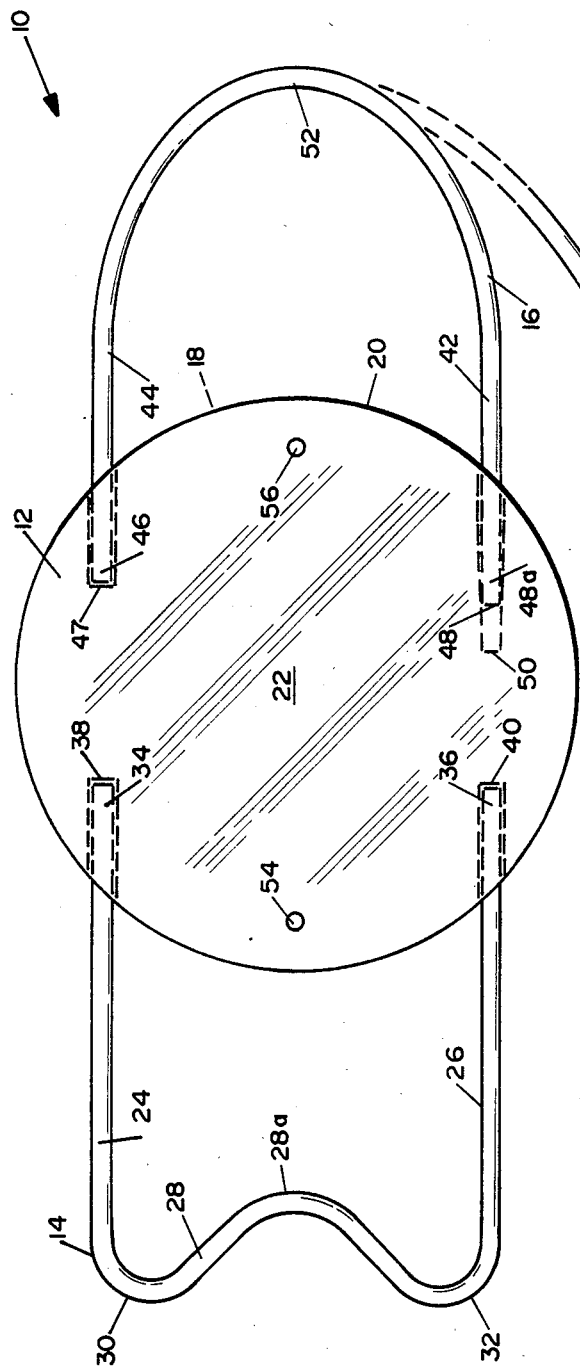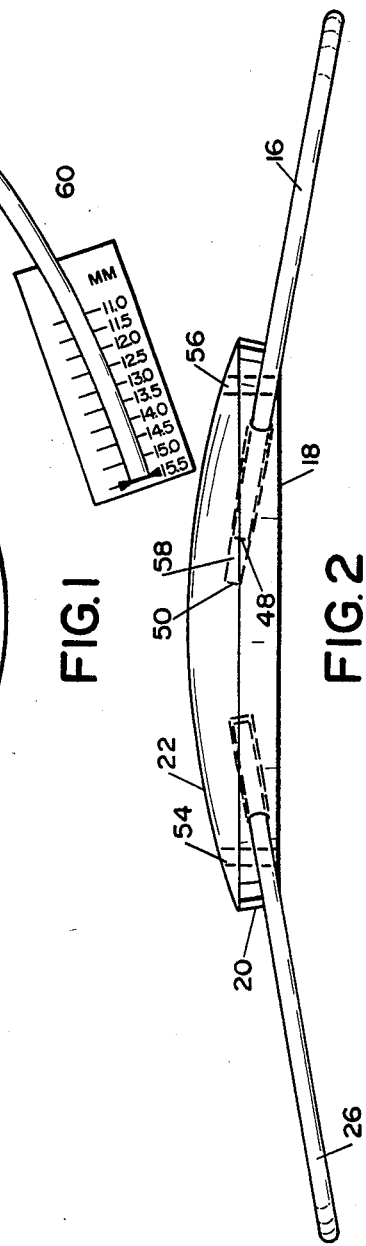

INTRAOCULAR LENS

BACKGROUND OF THE INVENTION

1. Field of the Invention

The present invention relates to an intraocular lens, and more particularly pertains to a lens which can be measured and adjusted for exact fit in a human eye.

2. Description of the Prior Art

Prior art lenses, especially anterior chamber lenses as well as posterior chamber lenses, are manufactured for finite discrete diameters of the eye. The ranges are usually from ten millimeters to fifteen millimeters in 0.5 millimeter increments.

The particular problem for the surgeon when implanting an intraocular lens is that he must not only have the correct diameter sized lens in the operating theater, but for purposes of assurance have the next larger and the next smaller size at hand. This is particularly burdensome not only upon the surgeon, but also upon the operating room personnel, the hospital stockroom, and the manufacturer and sales representative of the particular lens.

Sometimes when implanting a lens into the eye, it turns out that the diameter as measured by the surgeon does not correspond to the diameter of the lens. Also, the patient can be at an in-between diametrical measurement possibly not providing for the best placement of the intraocular lens into the eye.

The present invention overcomes the disadvantages of the prior art by providing a lens which is essentially one size, where one of the loops is heat-staked on one side and includes a free end which engages into a predrilled hole on the other side where the surgeon upon measurement of the eye cuts the proper amount of the loop off the free end for subsequent returning of the free end through the predrilled hole, providing for exact sizing of the lens to the eye.

SUMMARY OF THE INVENTION

The general purpose of the present invention is to provide a one-size intraocular lens, and more importantly to provide a lens which the surgeon can size in the operating theater to the eye by cutting a finite portion off the free end of one of the loops and then inserting that cut end into a predrilled hole, providing for exact sizing of the diameter of the lens to an individual's eye. The principles of the one-size intraocular lens are applicable to anterior chamber lenses as well as to posterior chamber lenses.

According to one embodiment of the present invention, there is provided an intraocular lens including a lens optic, two opposing flexible loops positioned about the lens optic, one of the loops having both ends secured to the lens optic, and the other loop having one end secured to the lens optic and an other end which is free and engageable into a predrilled hole of the lens optic, whereby the free end of the flexible loop can be sized by the surgeon in the operating theater by cutting off a finite portion and subsequently engaging into the predrilled hole, thereby sizing the lens optic to the individual's eye for a proper surgical placement therein. The lens optic can be a plano-convex lens and including a finite height for engagement of the loops. The loops can take a U-shape configuaration, a rounded configuration, or any other like geometrical configuration. The lens and the loops can be constructed from polymethylmethacrylate (PMMA), and the loops can be vaulted with respect to the lens optic. The loops of the present invention are substantially U-shaped at one end and indented at the other end of the U-shape.

One significant aspect and feature of the present invention is a lens which can be sized in the operating theater.

Another significant aspect and feature of the present invention is a lens which can be sized by the surgeon or operating room personnel in the operating theater, and only requires the use of surgical scissors or the like to cut off a predetermined portion of the free loop according to a chart supplied with the lens.

A further significant aspect and feature of the present invention is an intraocular lens which includes a template for cutting the free end of a loop to a predetermined length prior to mechanically and frictionally engaging the end of the loop into a tapered hole of the lens. This provides for a "one-size" fits all lens. The principles of the disclosure are applicable to anterior chamber lenses as well as posterior chamber lenses.

Having thus described the present invention, it is a principal object hereof to provide a one-sized intraocular lens.

One object of the present invention is to provide a lens which includes a free end of a loop which can be cut to size the lens according to a desired diametrical length for surgical placement in an individual's eye.

Another object of the present invention is to provide a free end of a loop which can be cut with ordinary surgical scissors by a surgeon or operating room personnel for sizing the lens to a predetermined diametrical length for placement in an individual's eye.

BRIEF DESCRIPTION OF THE DRAWINGS

Other objects and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 1 illustrates a top view of an intraocular lens, the present invention; and, FIG. 2 illustrates a side view of the lens of FIG. 1.

DESCRIPTION OF THE PREFERRED EMBODIMENTS

FIG. 1 illustrates a top view of a one-size intraocular lens 10, the present invention, including lens optic 12, a first U-shaped flexible loop 14, and a second U-shaped flexible loop 16 where both ends of the loops 14 and 16 are diametrically opposed to each other at opposite sides of the lens optic 12. The lens optic 12 includes a planar surface 18, a thin finite edge 20, and a convex surface 22, as also illustrated in FIG. 2. The lens optic 12 and the loops 14 and 16 are manufactured from a material such as polymethylmethacrylate (PMMA). The diametrical length of the lens optic 12 is in the range of four to seven millimeters and has varying dioptic powers in the range of nine to thirty. The loop 14 is secured at both ends to the lens optic and the loop 16 includes one secured end and one free end which engages into a predrilled hole, as now described in detail.

The loop 14 is a substantially U-shaped inward curved member having two opposing arms 24 and 26 connected by a base 28 having an inward curve 28a and including rounded corners 30 and 32. The loops are substantially 0.25 millimeters in diameter in a range of 0.08–0.5 millimeters and could include like vaulted ramp in each arm in an alternative to that shown in FIG. 2. The ends of the loops 34 and 36 are heat-staked to holes 38 and 40 through like and known processes in the art. The engagement between the ends of the loops and the holes is a frictional and mechanical engagement securing the ends of the loops to the respective holes, as illustrated in the figure.

Likewise, the loop 16 is provided with arms 42 and 44 where in this embodiment an end 46 engages into the hole 47 frictionally and is mechanically secured thereto. A free end 48 engages into a predrilled hole 50 for frictional engagement therein. The hole 50 can have a slight taper while the free end 48 is longer than required, providing for sizing of that end of the loop for subsequent engagement into the hole and diametrical sizing of the loops for surgical fitting and placement in an individual's eye. A portion of the end 48a is provided for excising from the end for subsequent sizing of the loop 16. For purposes of sizing the end 16 of the loop, the base 52 assumes a rounded configuration.

FIG. 2 illustrates a view taken along line 2—2 of FIG. 1 where all numerals correspond to those elements previously shown. Positioning hole 54 is illustrated. The tapered hole 50 is illustrated from a side view as well as the free end 48 of the lens. There is space 58 provided for movement of the free end as required and the end of the loop can move accordingly in the hole after surgical implantation and placement in the eye with no adverse effects to the individual.

The loops 14 and 16 are provided with a vault as known in the range of 0.5 mm. The loops will of course be configured for either a posterior chamber lens or an anterior chamber lens.

MODE OF OPERATION

The surgeon in the operating theater sizes the diameter of the patient's eye. According to a chart supplied with the lens, the surgeon is able to correlate the diameter of the individual's eye to the finite portion of the free end of the lens which is cut off with surgical scissors. A cutting guide is provided on an accompanying chart. The surgeon then inserts that cut free end 48 of the lens into the predrilled hole 50 for subsequent placement into the patient's eye.

The provision of sizing the lens in the operating theater negates the need for varying sizes of lenses in the operating theater as in prior surgical techniques, and provides for sizing of the lens directly by the surgeon in the operating theater, thus providing for an exact placement and implantation of the lens in the patient's eye.

FIG. 1 illustrates in dashed lines the free end of the loop 48 extending outward and away from the tapered hole 50 for cutting adjacent to a template 60. The template includes markings for diametrical lengths in the range of 11.0–15.5 mm dependent upon the length of the loop which is cut thereby providing the desired sized diametrical length of the lens. It is predetermined that the length cut from the free end provides the desired diametrical length and the amount cut is proportional thereto. While the templated is a preferred mode of sizing the lens through cutting of the free loop end, an alternative mode would be to place sizing marks on the free end of the loop where the sizing marks would correspond to the diametrical length of the lens. Scribe marks such as marks 62 illustrated in dashed lines could be provided on the free end of the loop in an alternative embodiment.

The template can be included in the sterile lens package containing the IOL for appropriate use in the operating room. The template can be formed of any suitable material and scribed accordingly. The template can even be formed into the lens package such as on an edge of the package such as on the end of a lens tray.

Various modifications can be made to the present invention without departing from the apparent scope thereof. For instance, the teachings of the present invention are applicable to any style of IOL, either type of IOL for the anterior chamber or posterior chamber, and for any type of loop configuration.

Having thus described the invention, what is claimed is:

1. Intraocular lens comprising:
   a. lens optic including a substantially rounded optic with two opposing surfaces;
   b. two opposing U-shaped loops, each of said loops formed of a smooth, round, cylindrical member, each of said loops including a rounded base, one of said loops secured into said lens optic; and,
   c. another of said loops having one end secured into said lens optic, and another free end of said loops for engagement into a predrilled hole in said lens optic, said free end of said loop being scribed for predetermined sizing whereby said free end can be sized accordingly for frictional engagement into said hole, thereby providing for a sized intraocular lens.

2. Lens of claim 1 wherein said lens is an anterior chamber lens.

3. Lens of claim 1 wherein said lens is a posterior chamber lens.

4. Lens of claim 1 wherein said loops are vaulted.

5. In combination, intraocular lens and template:
   a. intraocular lens including a lens optic of planoconvex surfaces, two opposing U-shaped loops, each of said loops formed of a smooth, round, cylindrical member, each of said loops including a substantially rounded base, one of said loops secured into said optic, another of said loops having one end secured into said lens optic, and another free end for engagement into a predrilled tapered hole in said lens optic; and,
   b. means for sizing said free end of said lens optic for subsequent placement and mechanical frictional engagement into said hole thereby providing a sized intraocular lens.

6. Combination of claim 5 wherein said sizing means comprises scribe marks on said free end of said loop whereby each scribe mark corresponds to a respective diametrical length of said lens.

7. Combination of claim 5 wherein said sizing means comprises a template corresponding to sizes to be cut for corresponding diametrical lengths.

8. Process for sizing diametrical length of an intraocular lens comprising the steps of:
   a. placing a free end of a loop of an intraocular lens next to a template;
   b. matching the diametrical length of a loop to a length on the template;
   c. cutting the portion of the free end of the loop at the diametrical length;
   d. engaging the cut end into a tapered hole for a mechanical frictional engagement of the end of the loop into the tapered hole thereby providing a sized intraocular lens.

* * * * *